US00PP23321P2

(12) United States Plant Patent
Deuter

(10) Patent No.: US PP23,321 P2
(45) Date of Patent: Jan. 8, 2013

(54) ***MISCANTHUS* PLANT NAMED 'MBS 0006'**

(50) Latin Name: *Miscanthus*
Varietal Denomination: MBS 0006, a.k.a 99m0029, 99m0006 or Flamingo Rest

(75) Inventor: Martin Deuter, Wanzleben (DE)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 13/385,459

(22) Filed: Feb. 22, 2012

Related U.S. Application Data

(60) Division of application No. 13/067,951, filed on Jul. 8, 2011, now abandoned, which is a continuation of application No. 12/584,496, filed on Sep. 4, 2009, now Pat. No. Plant 22,127, which is a continuation-in-part of application No. 12/387,444, filed on May 1, 2009, now Pat. No. Plant 22,033, and a continuation-in-part of application No. 12/387,429, filed on May 1, 2009, now Pat. No. Plant 22,047, and a continuation-in-part of application No. 12/387,437, filed on May 1, 2009, now abandoned.

(60) Provisional application No. 61/050,162, filed on May 2, 2008.

(51) Int. Cl.
*A01H 5/00* (2006.01)

(52) U.S. Cl. ..... Plt./384

(58) Field of Classification Search ..... Plt./384
See application file for complete search history.

(56) References Cited

U.S. PATENT DOCUMENTS

| | | | |
|---|---|---|---|
| PP13,008 | P2 | 9/2002 | Walsh |
| PP15,193 | P2 | 9/2004 | Smith et al. |
| PP16,197 | P2 | 1/2006 | Weiskott |
| PP18,161 | P2 | 10/2007 | Probst |
| PP22,033 | P2 | 7/2011 | Deuter |
| PP22,047 | P2 | 7/2011 | Deuter |
| PP22,127 | P2 | 9/2011 | Deuter |

*Primary Examiner* — Susan McCormick Ewoldt
(74) *Attorney, Agent, or Firm* — Cooley LLP; Jeffrey M. Libby; Yifan Mao

(57) ABSTRACT

A new and distinct cultivar of *Miscanthus* named 'MBS 0006' generally characterized by its rigorous growth rate, high biomass yield and high tiller density, and/or improved cold tolerance.

5 Drawing Sheets

Latin name of genus: *Miscanthus.*
Varietal denomination: 'MBS 0006', a.k.a. '99m0029', '99m0006' or 'Flamingo Rest'.

BACKGROUND

The present disclosure relates to a new and distinct cultivar of hybrid *Miscanthus* originated as a polycross of *Miscanthus sinensis* with other *Miscanthus* species and will be referred to hereafter by its cultivar name 'MBS 0006'. 'MBS 0006' represents a new cultivar of *Miscanthus* species, a perennial grass which is grown for biomass production, landscape use, ornamental value, and cold tolerance.

Seeds of an open-pollinated *Miscanthus sinensis* plant in a natural *Miscanthus* habitat at Shirakawa-Gun, Honshu, Japan were planted and screened in a cultivated selection field at Klein-Wanzleben, Germany. The selection field was utilized for seed increase of superior genotypes derived from the original plant selection. Additional recurrent selection in the newly derived, finite population was utilized to derive additional selection pressure for line improvement.

*Miscanthus sinensis* is self incompatible. Presumably, the *Miscanthus sinensis* plant in the natural habitat in Japan became pollinated by other *Miscanthus* plants, hence it could be regarded as a polycross of *M. sinensis* plants. Therefore, its continued lineage/pedigree was derived from seed collected on this plant selection. The open pollinated seed from the population plant selection was a bulk collection of half-sib lines (genotypes) from that mother plant, and were planted for advanced recurrent selection in an organized *Miscanthus sinensis* breeding nursery at Klein Wanzleben, Germany. The isolated poly-cross population ('114SW') at Klein Wanzleben produced seed on various high performing biomass types. Seed collected from this population was named '95s0043' and was again planted at Klein Wanzlchlen for recurrent selection and advancement of improved biomass clonal lines. From this population an individual plant was selected for vigorous growth, high biomass and cold tolerance potential. The accession was named '99m0029', a.k.a. 'MBS 0006', '99m0006', or 'Flamingo Rest'.

The plant was asexually reproduced from sterile rhizome buds in Klein-Wanzleben, Germany by the inventor. The shoot material was propagated on rooting media and the rooted plantlets were planted into pots in the greenhouse. The plants were planted into the field after one cold period. The characteristics of this cultivar have been determined to be stable and are reproduced true to type in successive generations. 'MBS 0006' was transferred to US via APHIS quarantine inspection regulations and was established for performance trials in the US. 'MBS 0006' performance trials include biomass yield and trait characteristic observations. 'MBS 0006' has been evaluated in mutli-entry, replicated performance trials. These trials ranged across three diverse US locations targeted as US biomass growing regions of the country.

SUMMARY OF THE INVENTION

The new cultivar 'MBS 0006' has not been observed under all possible environmental conditions. The phenotype may vary somewhat with variations in temperature, day-length, light intensity, soil types, and water and fertility levels without, however, any significant variance in genotype.

The following traits have been repeatedly observed and are determined the basic characteristics of 'MBS 0006', which in combination distinguish this *Miscanthus sinensis* hybrid from the known *Miscanthus*×*giganteus* and other ornamental *M. sinensis* forms. Plants for the botanical measurements in the present application are two and three-year-old plants. These plants would be considered as mature plants.

1. Vigorous growth
2. Plant height: approximately 3 m at or above 35 deg N latitude and about 2.5 m at or below 35 deg Northern latitude.
3. Green leaves, no colored stripes are present, but green leaves have a creamy white leaf mid rib characteristic of *M. sinensis* biomass genotypes.
4. High biomass yield compared to several *Miscanthus* cultivars.
5. High culm thickness.
6. Excellent area of adaptation for both warm and cold climates of biomass growing regions.

'MBS 0006' can be distinguished from the *Miscanthus* cultivars Strictus (not patented), Super Stripe (U.S. Plant Pat. No. 18,161), Gold Bar (U.S. Plant Pat. No. 15,193), Little Zebra (U.S. Plant Pat. No. 13,008) and Mysterious Maiden (U.S. Plant Pat. No. 16,197) in that 'MBS 0006' has no stripes or colored bands on its leaves.

In side by side comparisons conducted in Klein-Wanzleben, Germany, 'MBS 0006' is more vigorous than other ornamental *M. sinensis*. 'MBS 0006' has taller culms but demonstrates less lodging; hence it has stronger culms. 'MBS 0006' culms are also very straight and medium upright in appearance when compared to other *sinensis* genotypes. It shows excellent winter survival at all northern and southern locations tested.

The plant flowers and produces fertile seeds. 'MBS 0006' develops inflorescences and viable seeds under optimal growing conditions. However, 'MBS 0006' is 98% self incompatible. Therefore, it requires cross pollination with different *Miscanthus* genotypes to produce viable seeds. The plant can be propagated by rhizomes or from meristem in tissue culture or adventitious root and shoot development under ideal vegetative propagation environments.

BRIEF DESCRIPTION OF THE DRAWINGS

The accompanying color photographs illustrate the overall appearance and distinct characteristics of the new *Miscanthus* cultivar 'MBS 0006'.

The photograph in FIGS. 1 and 2 illustrate the overall growth habit and appearance of 'MBS 0006' at winter dormancy and in the summer, respectively, in Tifton, USA.

FIG. 3 illustrates midseason green color, glabrous leaf texture and the white mid-rib characteristic to 'MBS 0006'.

FIGS. 4 and 5 illustrate culm/cane thickness of midseason and dormant 'MBS 0006'. The culm width of 'MBS 0006' is a unique characteristic among the comparison group in that it is significantly thicker in this yield trial measurement (Tables 1-4).

FIGS. 6, 7, and 8 illustrate mid-season plant and panicle development at Tifton, Ga. in July.

DETAILED BOTANICAL DESCRIPTION OF THE PLANT

'MBS 0006' has not been observed under all possible environmental conditions, and the phenotype may vary significantly with variations in environment. It has been observed under several environmental conditions, including mid, central and southern regions of the US and Klein Wanzleben, Germany. The following observations, measurements, and comparison describe this plant as grown at Klein-Wanzleben, Germany, when grown in the field. All observations were recorded during the plant's dormant season (April). The color determination is in accordance with The 1995 R.H.S. Colour Chart of The Royal Horticultural Society, London, England, except where general color terms of ordinary dictionary significance are used. Plants for the botanical measurements in the present application are two and three-year-old plants. These plants would be considered as mature plants.

Additional and most relevant performance data included in this application includes observations, measurements and comparisons describing this plant that were recorded in fields grown at Tilton, Ga., Schocho, Ky., and Lafayette, Ind. Reported data exemplifies this genotype's ability to perform as a high biomass producing perennial crop for commercial markets. Therefore, beyond descriptive data, yield traits are presented and compared to commercial and pre-commercial cultivars associated with this market.

Botanical classification: 'MBS 0006' is a hybrid genotype derived from selected polycrossed *M. sinensis* plants. 'MBS 0006' is a diploid (2×) with chromosome complement of 38.

Common name: Maiden grass.

Parentage: Polycross of *M. sinensis* originated from Japan and other unknown *Miscanthus* species originated from Japan. Plant selections from that original population were recombined in a new poly cross of which the parental plant selection is indicated in FIG. 1.

General description:

*Blooming period.*—'MBS 0006' may bloom in mid summer in the southern US and late summer to mid fall in central US. It maintains a relatively indeterminate growth habit regarding continuous culm and panicle production until early frost in the fall. Plants grown in northern locations close to and well above 40 deg North bloom during early to late fall. Blooms are retained for a period of time, but blooming completely shuts down after frost.

*Plant habit.*—Herbaceous, tuft forming, biomass grass with upright culms, with 15-17 leaves per culm.

*Height and spread.*—Top leaf height about 2.9-3.0 meters.

*Hardiness.*—Productive growth in Klein-Wanzleben (north central), Germany and Ontario, Canada. It has very good drought and heat resistant in southern regions below 30 deg N latitude.

*Culture.*—Best in sandy loam, well-drained soil, higher yields at higher soil fertility.

*Diseases and pests.*—In United States 'MBS 0006' has shown excellent resistance to *Miscanthus* blight when compared to the public check variety *M. giganteus* cv. Illinois.

*Root description.*—Fibrous, well branched and dense. Fast-developing creeping rhizomes with shoots arising about 1-2 feet from base of the culms depending on field plant density.

Growth and propagation:

*Propagation.*—By culm division, in vitro culture, from rhizomes or meristem. Seed can be harvested and propagated if allowed to pollinate with other *Miscanthus* genotypes/parents for crosses or seed production.

*Growth rate.*—Vigorous.

Culm (stem) description: (Plant ages for data below are from two and three-year-old plants. They would be considered mature plants.)

*General*.—Cylindrical, pithy, reed-like, erect, sheathed. Culm thickness is significant for this *M. sinenesis* genotype.

*Culm aspect*.—Rigid and held erect, none are cascading.

*Culm length*.—Average about 2.5-3 m.

*Culm diameter*.—Average about 6.7-7.8 mm.

*Plant width*.—The average plant width is dependent on field planting density, but as a stand alone plant its width can be about 2-3 m.

*Plant height*.—Average about 2.7-3.0 meters.

*Culm color* (*dormant season*).—Yellowish (2D), lower internodes partly reddish (53A), and vary with intensity depending on locations and growing conditions. The rate on which the culm color changes is dependent on location and growing conditions.

*Compressed circumference*.—About 120 cm on a 2 year old plant, fully compressed with standard compression belt.

*Culm surface texture*.—Culm is glabrous.

*Internode length*.—Varies by location on plant and growing environment (about 5 cm to about 15 cm).

*Ligule*.—Membranous, about 5 mm (*M. giganteus* cv Illinois is 2.5-3 mm), color reddish 145B, border 58A, longest hair is about 4 mm (*M. giganteus* cv Illinois is 1 mm), encircles the entire culm, inner surface is glabrous, glabrous outer surface, and side.

*Cold hardiness*.—Survives in Germany and Canada.

*Culture*.—Best in sandy loam, well-drained soil, higher yields in warmer climates and higher soil fertility.

Foliage description:

*Leaf shape*.—Linear.

*Leaf margin*.—Green 140A.

*Leaf division*.—Simple.

*Leaf apex*.—Acuminate.

*Leaf aspect*.—Emerging leaves are erect, blades are convex, leaf angle of younger leaves is 50°, leaf angle of older leaves is 5°, color code 154C.

*Leaf length and width*.—About 2.5 cm in width and about 50 cm in length.

*Leaf base*.—Sheathed.

*Leaf attachment*.—Sheathed.

*Leaf arrangement*.—Alternate.

*Leaf color* (*during growing season*).—Green, white midrib, green color code is 140A.

Flower description:

*General description*.—Compact, fan-shaped panicle terminating from each culm in mid to late July through September in the south and September to late October in the north. It is composed of numerous slender, silky aggregate racemes.

*Angle of raceme*.—Varies with age of panicle — see FIGS. 7 and 8.

*Lastingness of inflorescence*.—For emergence until panicle dehiscence: about 2.5 months.

*Fragrance*.—None detected.

*Panicle size*.—Average of about 12-15 cm in length and about 8 cm in width at seed maturation stage.

*Panicle color*.—Varies from 154A to 2D at maturity. The intensity of these color grades depends on location and growing conditions.

*Spikelet description*.—Spikelets in pairs.

*Spikelet color*.—154B.

*Spikelet size*.—About 8 mm in length and about 2 mm in width (excluding hairs).

*Spikelet hairs*.—About 14 mm in length, 158C in color.

*Awn size*.—About 2 mm.

Reproductive organ description:

*Androecium*.—Anthers about 5 mm in length, and about 0.5 mm in width, reddish purple in color, 187A.

*Gynoecium*.—Stigma color is purple 186C, about 4 mm in length and about 0.5 mm in width.

*Caryopsis*.—Produces fertile seeds.

REPRODUCTION

'MBS 0006' has a small elliptical seed, which is a heavy anemochore with an average seed weight of about 0.92 mg, a chamaephyte (buds permanently above ground) life form, with an annual seed production of 0-2400 seeds per plant depending upon pollen source availability. Healthy seed is clear amber to dark brown (RHS code 166B).

YIELD

The average yield of 'MBS 0006' compared to appropriate commercial and pre-commercial check cultivars are summarized in Tables 1 through 4.

Variety comparisons were selected for this patent application based on commercial and pre-commercial genotypes with similar and competitive yields levels and uniqueness to sister lines of similar family. Comparison to *M. sinensis* cultivars that are commercially available are only used in reference to morphological phenotype because available cultivars are not biomass types of varieties.

Although 'MBS 0006' was not the highest biomass yielder across or within locations it was always in the top 10% of the full trial analysis. In the truncated analysis which included entries of relevance for biomass comparisons 'MBS 0006' was competitive with the best pre-commercial MBI cultivars, and out-performed all of the most competitive *sinensis* lines. A key biomass trait is culm thickness and 'MBS 0006' has a significantly thicker culm than the other entries in the test. This trait is important in that it can bring value to biomass yield parameters in *Miscanthus* as well as to its utility in breeding programs.

For Tables 1 to 4, all traits presented were measured at and harvest during winter dormancy growth stage. Definitions for the terms and abbreviations are:

1. Biomass dt/ac: Average post senescence, and dormancy harvest measured in dry tons per acre.
2. PH: Average total plant height measured in cm from soil surface to base of panicle (5 culm subsample per plot).
3. Culm Dia: Average culm diameter measured in mm across mid section of culm
4. Culm Density Rating: 1-5, where 1 refers to the least culm density visually observed relative to the trial entries, and 5 is the highest culm density visually observed relative to trial entries. A rating of 3 represents average and medium culm density relative to trial entries.
5. Biomass Rating: 1-5, where 1 is the least observed biomass appearance relative to trial entries, and 5 is the highest biomass observed relative to trial entries. A rating of 3 represents average and medium biomass relative to trial entries.
6. Leaf Retention: 1-5, where 1 is the least observed leaves retained on the plant after fall and winter dormancy relative to trial entries, and 5 is the highest observed leaves retained on the plant after fall and winter dormancy relative to trial entries. A rating of 3 represents average and medium leaf retention relative to trial entries.
7. Lodge: 1-5, where 1 is the least observed plant/culm lodging from base of the plant after fall and winter dormancy relative to trial entries, and 5 is the highest observed plant/culm lodging from base of the plant after fall and winter dormancy. A rating of 3 represents average and medium lodging relative to trial entries.

TABLE 1

Combined location yield summary for 'MBS 0006' ('99m0006') performance on two-year established , *Miscanthus* field plots located at Tifton, GA, Schocho, KY and Lafayette, IN. APHIS *Miscanthus* spp. Diversity Trial: 2nd Year, Mean Yield Data, 3 Locations Combined.

| | | | | | 3 Locations Combined analysis: TIF, LAF, SCKY - February-March harvest | |
|---|---|---|---|---|---|---|
| | | | | | Biomass Yield dt/ac | |
| Entry | Material Name | Species | 3 Locs Combined | Rk | Tifton | Rk |
| 11 | MBX-006 | *M.sa*//*Msi* | 6.4 | 1 | 7.5 | 1 |
| 1 | Nagara | M.xg: 3x | 5.1 | 2 | 4.8 | 2 |
| 9 | MBX-004 | *M.sa*//*Msi* | 4.9 | 3 | 3.2 | 8 |
| 8 | Lake Erie | *M.sa*//*Msi* | 4.8 | 6 | 4.5 | 4 |
| 5 | 99m0006 | *M.si* | 4.5 | 4 | 4.6 | 3 |
| 10 | MBX-005 | *M.sa*//*Msi* | 4.0 | 5 | 4.3 | 6 |
| 2 | Illinois | M.xg: 3x | 3.5 | 7 | 1.5 | # |
| 4 | 99m0005 | *M.si* | 3.3 | 8 | 3.3 | 7 |
| 7 | 99m0044 | *M.si* | 2.5 | 9 | 4.3 | 5 |
| 3 | 99m0003 | *M.si* | 2.3 | 10 | 0.5 | # |
| 6 | 99m0029 | *M.si* | 1.8 | 11 | 1.7 | 9 |
| | Mean | | 3.9 | | 3.2 | |
| | LSD(.05) | | 1.8 | | 1.9 | |
| | CVErr | | 24.5 | | 27.8 | |
| | CVExL | | 15.6 | | na | |

| | | 3 Locations Combined analysis: TIF, LAF, SCKY - February-March harvest | | | | | |
|---|---|---|---|---|---|---|---|
| | | | | | | Yield Traits | |
| | | Biomass Yield dt/ac | | | | | Culm |
| Entry | Material Name | Lafayette | Rk | Schochoh | Rk | PH (cm) | Dia (mm) |
| 11 | MBX-006 | 4.0 | 5 | 7.8 | 1 | 263 | 7.0 |
| 1 | Nagara | 4.6 | 2 | 5.8 | 3 | 257 | 5.6 |
| 9 | MBX-004 | 5.6 | 1 | 5.9 | 2 | 258 | 5.5 |
| 8 | Lake Erie | 4.6 | 3 | 5.4 | 5 | 208 | 6.3 |
| 5 | 99m0006 | 4.1 | 4 | 4.7 | 6 | 265 | 8.5 |
| 10 | MBX-005 | 3.3 | 7 | 4.4 | 7 | 236 | 7.2 |
| 2 | Illinois | 3.5 | 6 | 5.4 | 4 | 229 | 5.9 |
| 4 | 99m0005 | 3.2 | 8 | 3.4 | 9 | 236 | 7.5 |
| 7 | 99m0044 | 1.4 | 10 | 1.9 | # | 216 | 6.2 |
| 3 | 99m0003 | 3.1 | 9 | 3.3 | # | 209 | 7.5 |
| 6 | 99m0029 | 0.0 | 11 | 3.8 | 8 | 265 | 5.6 |
| | Mean 3.7 | | | 2.5 | | 237.7 | 6.6 |
| | LSD(.05) 2.4 | | | 1.8 | | 12.4 | 1.3 |
| | CVErr 37.5 | | | 37.0 | | 5.5 | 12.1 |
| | CVExL na | | | na | | 5.2 | 20.0 |

TABLE 1-continued

Combined location yield summary for 'MBS 0006' ('99m0006') performance on two-year established , *Miscanthus* field plots located at Tifton, GA, Schocho, KY and Lafayette, IN. APHIS *Miscanthus* spp. Diversity Trial: 2nd Year, Mean Yield Data, 3 Locations Combined.

| | | 3 Locations Combined analysis: TIF, LAF, SCKY - February-March harvest Ratings 1-5 | | | |
|---|---|---|---|---|---|
| Entry | Material Name | Culm Density | Biomass Rating | Leaf Retention | Lodge |
| 11 | MBX-006 | 4 | 4.4 | 4 | 0 |
| 1 | Nagara | 4 | 4.2 | 4 | 1 |
| 9 | MBX-004 | 4 | 3.8 | 4 | 0 |
| 8 | Lake Erie | 4 | 3.8 | 5 | 0 |
| 5 | 99m0006 | 3 | 4.3 | 4 | 1 |
| 10 | MBX-005 | 4 | 3.9 | 4 | 0 |
| 2 | Illinois | 4 | 3.6 | 4 | 0 |
| 4 | 99m0005 | 3 | 3.4 | 4 | 0 |
| 7 | 99m0044 | 2 | 2.8 | 3 | 1 |
| 3 | 99m0003 | 2 | 2.7 | 4 | 0 |
| 6 | 99m0029 | 3 | 3.1 | 4 | 1 |
| | Mean 3.0 | | 3.7 | 4.0 | 0.0 |
| | LSD(.05) 0.5 | | 0.6 | 1.0 | 0.0 |
| | CVErr 12.0 | | 12.7 | 7.8 | |
| | CVExL 12.2 | | 17.1 | 13.2 | |

TABLE 2

Yield summary for 'MBS 0006' ('99m0006') performance on two-year established *Miscanthus* field plots, located at Tifton, GA, growing season. API-US *Miscanthus* spp. Diversity Trial: 2nd Year Mean Yield Data at Tifton, GA.

| | | | Tifton, GA: February 2nd Yr Harvest Yield Traits | | | |
|---|---|---|---|---|---|---|
| | Material | | dt/acre | | PH | Culm Dia |
| Entry | Name | Species | Tifton | Rk | (cm) | (mm) |
| 11 | MBX-006 | *Msa*//*Msi* | 7.5 | 1 | 228 | 6.2 |
| 1 | Nagara | *Mxg*:*Mis* X *giganteus* | 4.8 | 2 | 204 | 3.6 |
| 5 | 99m0006 | *Msi*:*Mis sinensis* | 4.6 | 3 | 220 | 6.8 |
| 8 | Lake Erie | *Msa*//*Msi* | 4.5 | 4 | 181 | 4.5 |
| 7 | 99m0044 | *Msi*:*Mis sinensis* | 4.3 | 5 | 192 | 4.6 |
| 10 | MBX-005 | *Msa*//*Msi* | 4.3 | 6 | 219 | 6.6 |
| 4 | 99m0005 | *Msi*:*Mis sinensis* | 3.3 | 7 | 207 | 6.4 |
| 9 | MBX-004 | *Msa*//*Msi* | 3.2 | 8 | 211 | 4.8 |
| 6 | 99m0029 | *Msi*:*Mis sinensis* | 1.7 | 9 | 193 | 5.3 |
| 2 | Illinois | *Mxg*:*Mis* X *giganteus* | 1.5 | 10 | 196 | 4.2 |
| 3 | 99m0003 | *Msi*:*Mis sinensis* | 0.5 | 11 | 157 | 5.1 |
| | Mean | | 3.7 | | 201.0 | 5.3 |
| | LSD(.05) | | 3.2 | | 35.1 | 2.0 |
| | CVErr | | 51.8 | | 10.3 | 22.6 |

TABLE 2-continued

Yield summary for 'MBS 0006' ('99m0006') performance on two-year established *Miscanthus* field plots, located at Tifton, GA, growing season.
API-US *Miscanthus* spp. Diversity Trial:
2nd Year Mean Yield Data at Tifton, GA.

| | | | Tifton, GA: February 2nd Yr Harvest Yield Traits | | |
|---|---|---|---|---|---|
| | | | Ratings 1-5 | | |
| Entry | Material Name | Species | Culm Density | Biomass Rating | Leaf Retention |
| 11 | MBX-006 | *Msa//Msi* | 4 | 5.0 | 5 |
| 1 | Nagara | *Mxg:Mis* X *giganteus* | 3 | 3.5 | 5 |
| 5 | 99m0006 | *Msi:Mis sinensis* | 2 | 4.7 | 4 |
| 8 | Lake Erie | *Msa//Msi* | 4 | 4.0 | 5 |
| 7 | 99m0044 | *Msi:Mis sinensis* | 2 | 3.3 | 4 |
| 10 | MBX-005 | *Msa//Msi* | 5 | 4.0 | 5 |
| 4 | 99m0005 | *Msi:Mis sinensis* | 3 | 3.3 | 5 |
| 9 | MBX-004 | *Msa//Msi* | 4 | 3.0 | 5 |
| 6 | 99m0029 | *Msi:Mis sinensis* | 2 | 2.7 | 4 |
| 2 | Illinois | *Mxg:Mis* X *giganteus* | 3 | 3.0 | 4 |
| 3 | 99m0003 | *Msi:Mis sinensis* | 1 | 1.3 | 4 |
| | Mean | | 3.0 | 3.4 | 5.0 |
| | LSD(.05) | | 1.0 | 1.3 | 1.0 |
| | CVErr | | 27.4 | 22.3 | 12.5 |

TABLE 3

Yield summary for 'MBS 0006' ('99m0006') performance on two-year established *Miscanthus* field plots, located at Lafayette, IN, growing season.
APHIS *Miscanthus* spp. Diversity Trial:
2nd Year Mean Yield Data at Lafayette, IN

| | | | Lafayette, IN: March, 2nd Yr Harvest Yield Traits | | | |
|---|---|---|---|---|---|---|
| | | | dt/acre | | | Culm |
| Entry | Material Name | Species | Lafay-ette | Rk | PH (cm) | Dia (mm) |
| 9 | MBX-004 | *Msa//Msi* | 5.6 | 1 | 228 | 6.8 |
| 1 | Nagara | *Mxg:Mis* X *giganteus* | 4.6 | 2 | 236 | 7.6 |
| 8 | Lake Erie | *Msa//Msi* | 4.6 | 3 | 165 | 7.2 |
| 5 | 99m0006 | *Msi:Mis sinensis* | 4.1 | 4 | 232 | 11.2 |
| 11 | MBX-006 | *Msa//Msi* | 4.0 | 5 | 225 | 8.4 |
| 2 | Illinois | *Mxg:Mis* X *giganteus* | 3.5 | 6 | 199 | 8.0 |
| 10 | MBX-005 | *Msa//Msi* | 3.3 | 7 | 194 | 9.1 |
| 4 | 99m0005 | *Msi:Mis sinensis* | 3.2 | 8 | 183 | 8.6 |
| 3 | 99m0003 | *Msi:Mis sinensis* | 3.1 | 9 | 177 | 10.2 |
| 7 | 99m0044 | *Msi:Mis sinensis* | 1.4 | 10 | 168 | 4.4 |
| 6 | 99m0029 | *Msi:Mis sinensis* | 0.0 | 11 | 0 | 0.0 |
| | Mean | | 3.7 | | 200.7 | 8.1 |
| | LSD(.05) | | 2.4 | | 46.4 | 3.1 |
| | CVErr | | 37.5 | | 13.6 | 22.3 |

TABLE 3-continued

Yield summary for 'MBS 0006' ('99m0006') performance on two-year established *Miscanthus* field plots, located at Lafayette, IN, growing season.
APHIS *Miscanthus* spp. Diversity Trial:
2nd Year Mean Yield Data at Lafayette, IN

| | | | Lafayette, IN: March, 2nd Yr Harvest Yield Traits | | |
|---|---|---|---|---|---|
| | | | Ratings 1-5 | | |
| Entry | Material Name | Species | Culm Density | Bio-mass Rating | Leaf Retention |
| 9 | MBX-004 | *Msa//Msi* | 4 | 4.0 | 3 |
| 1 | Nagara | *Mxg:Mis* X *giganteus* | 4 | 4.0 | 3 |
| 8 | Lake Erie | *Msa//Msi* | 4 | 4.0 | 4 |
| 5 | 99m0006 | *Msi:Mis sinensis* | 3 | 4.0 | 3 |
| 11 | MBX-006 | *Msa//Msi* | 4 | 4.0 | 3 |
| 2 | Illinois | *Mxg:Mis* X *giganteus* | 4 | 3.0 | 4 |
| 10 | MBX-005 | *Msa//Msi* | 4 | 3.0 | 3 |
| 4 | 99m0005 | *Msi:Mis sinensis* | 3 | 3.0 | 4 |
| 3 | 99m0003 | *Msi:Mis sinensis* | 3 | 3.0 | 4 |
| 7 | 99m0044 | *Msi:Mis sinensis* | 2 | 2.0 | 2 |
| 6 | 99m0029 | *Msi:Mis sinensis* | 0 | 0.0 | 0 |
| | Mean | | 3.0 | 3.0 | 3.0 |
| | LSD(.05) | | 1.0 | 2.0 | 1.0 |
| | CVErr | | 22.0 | 29.5 | 16.3 |

TABLE 4

Yield summary for 'MBS 0006' ('99m0006') performance on two-year established *Miscanthus* field plots, located at Schocho, KY, growing season.
APHIS *Miscanthus* spp. Diversity Trial:
2nd Year Mean Yield Data at Schochoh, KY

| | | | Schocho, KY: March, 2nd Yr Harvest Yield Traits | | | |
|---|---|---|---|---|---|---|
| | Material | | dt/acre | | PH | Culm Dia |
| Entry | Name | Species | Schocho | Rk | (cm) | (mm) |
| 11 | MBX-006 | *Msa//Msi* | 7.8 | 1 | 335 | 6.5 |
| 9 | MBX-004 | *Msa//Msi* | 5.9 | 2 | 335 | 4.8 |
| 1 | Nagara | *Mxg:Mis* X *giganteus* | 5.8 | 3 | 330 | 5.5 |
| 2 | Illinois | *Mxg:Mis* X *giganteus* | 5.4 | 4 | 292 | 5.6 |
| 8 | Lake Erie | *Msa//Msi* | 5.4 | 5 | 279 | 7.1 |
| 5 | 99m0006 | *Msi:Mis sinensis* | 4.7 | 6 | 342 | 7.7 |
| 10 | MBX-005 | *Msa//Msi* | 4.4 | 7 | 294 | 6.0 |
| 6 | 99m0029 | *Msi:Mis sinensis* | 3.8 | 8 | 337 | 6.0 |
| 4 | 99m0005 | *Msi:Mis sinensis* | 3.4 | 9 | 318 | 7.6 |
| 3 | 99m0003 | *Msi:Mis sinensis* | 3.3 | 10 | 294 | 7.1 |
| 7 | 99m0044 | *Msi:Mis sinensis* | 1.9 | 11 | 288 | 7.5 |
| | Mean | | 2.5 | | 313.1 | 6.5 |
| | LSD(.05) | | 1.8 | | 33.1 | 1.8 |
| | CVErr | | 37.0 | | 6.3 | 16.3 |

TABLE 4-continued

Yield summary for 'MBS 0006' ('99m0006') performance on two-year established *Miscanthus* field plots, located at Schocho, KY, growing season.
APHIS *Miscanthus* spp. Diversity Trial:
2nd Year Mean Yield Data at Schochoh, KY

| | | | Schocho, KY: March, 2nd Yr Harvest Yield Traits | | |
|---|---|---|---|---|---|
| | | | Ratings 1-5 | | |
| Entry | Material Name | Species | Culm Density | Biomass Rating | Leaf Retention |
| 11 | MBX-006 | *Msa//Msi* | 5 | 4.3 | 5 |
| 9 | MBX-004 | *Msa//Msi* | 4 | 4.3 | 5 |
| 1 | Nagara | *Mxg*:*Mis* X *giganteus* | 4 | 4.7 | 5 |
| 2 | Illinois | *Mxg*:*Mis* X *giganteus* | 4 | 3.5 | 5 |
| 8 | Lake Erie | *Msa//Msi* | 5 | 3.7 | 5 |
| 5 | 99m0006 | *Msi*:*Mis sinensis* | 3 | 4.3 | 4 |
| 10 | MBX-005 | *Msa//Msi* | 4 | 3.7 | 5 |
| 6 | 99m0029 | *Msi*:*Mis sinensis* | 4 | 3.6 | 4 |
| 4 | 99m0005 | *Msi*:*Mis sinensis* | 3 | 4.0 | 4 |
| 3 | 99m0003 | *Msi*:*Mis sinensis* | 3 | 4.0 | 4 |
| 7 | 99m0044 | *Msi*:*Mis sinensis* | 2 | 3.0 | 2 |
| | Mean | | 4.0 | 3.9 | 4.0 |
| | LSD(.05) | | 1.0 | 1.4 | 1.0 |
| | CVErr | | 14.7 | 21.9 | 13.1 |

The invention claimed is:

1. A new and distinct cultivar of *Miscanthus* plant named 'MBS 0006' substantially as herein shown and described.

* * * * *

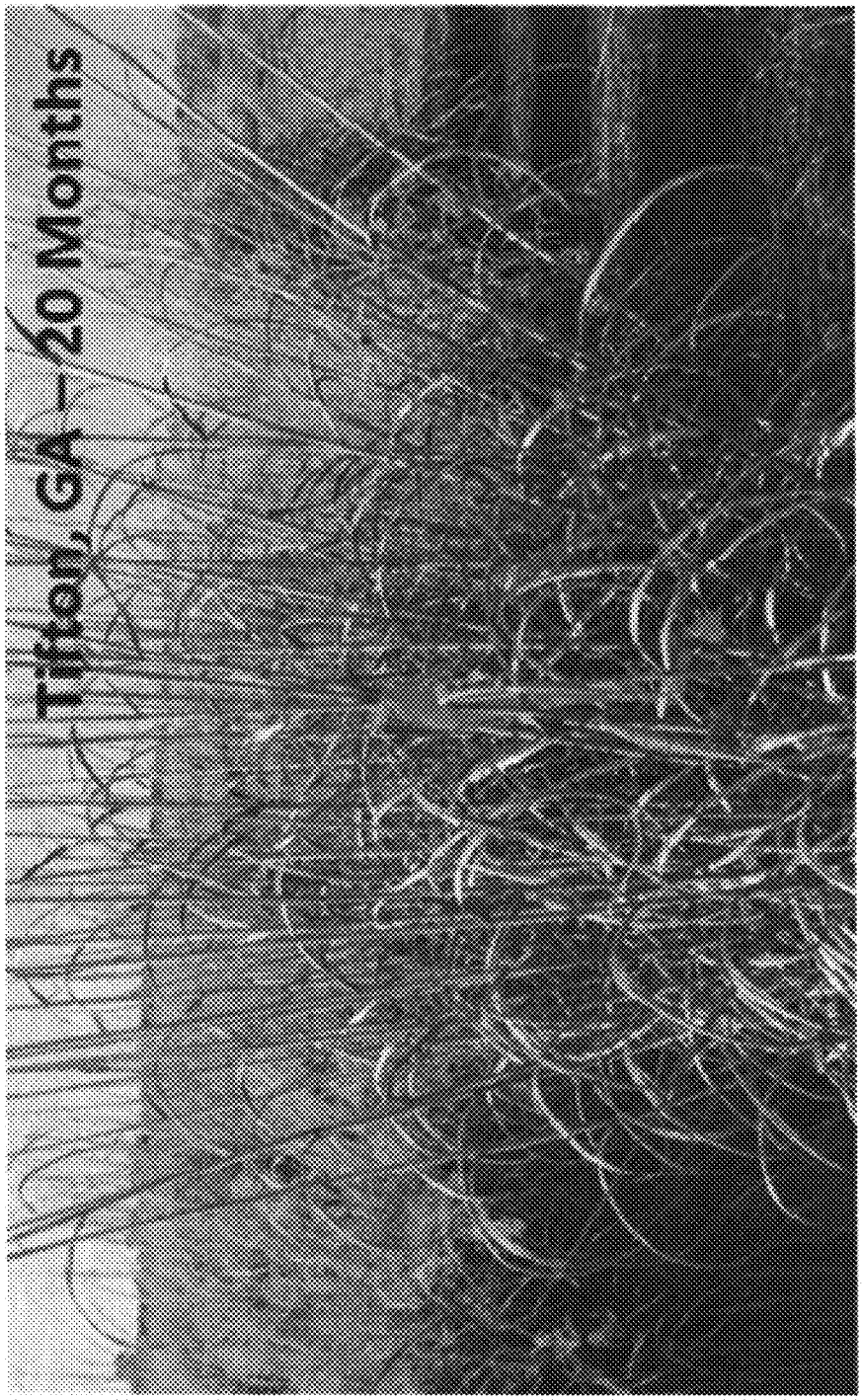
Figure 1. 'MBS 0006' July, 2nd growing season, pre-harvest

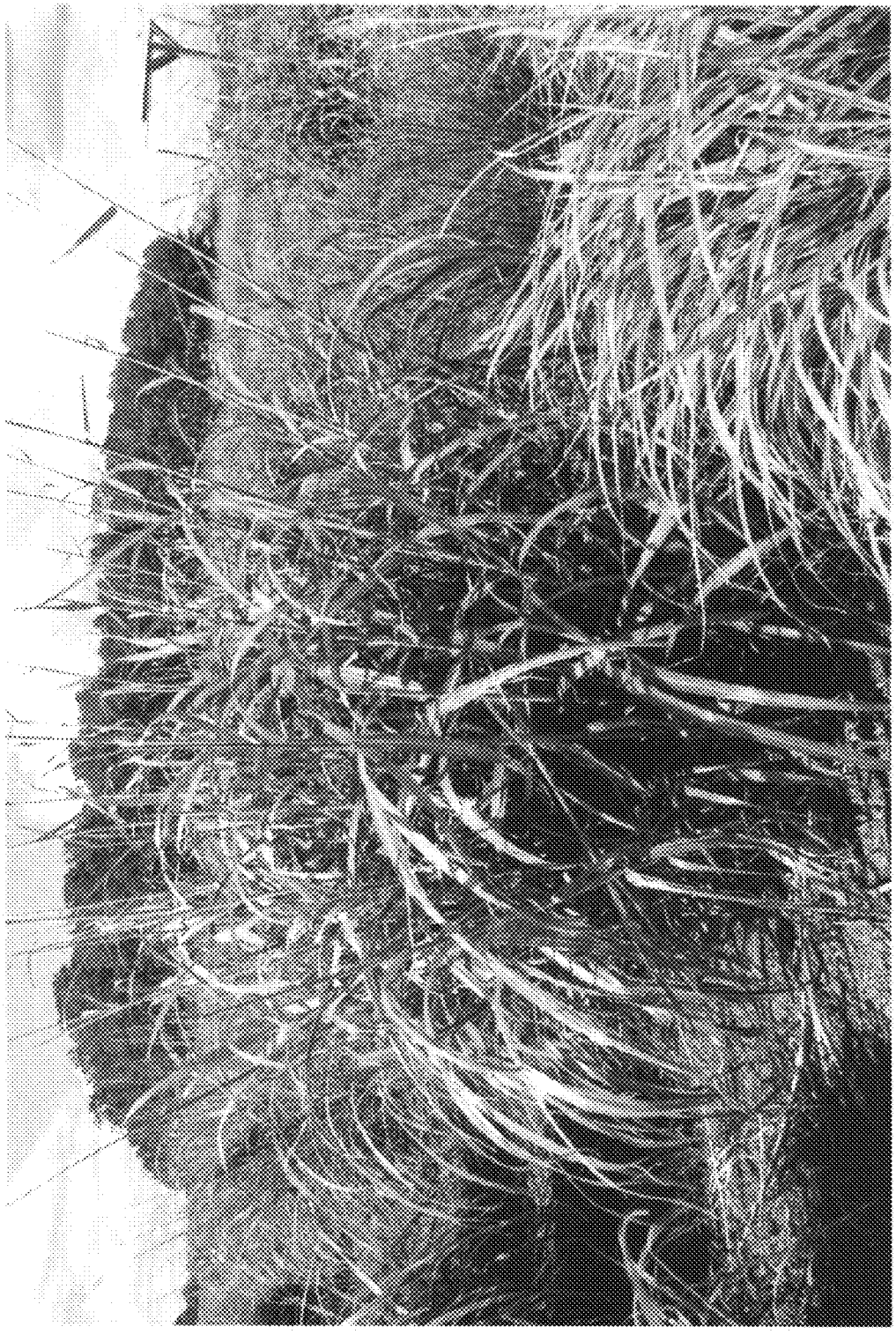
Figure 2. 'MBS 0006' July, 3rd growing season

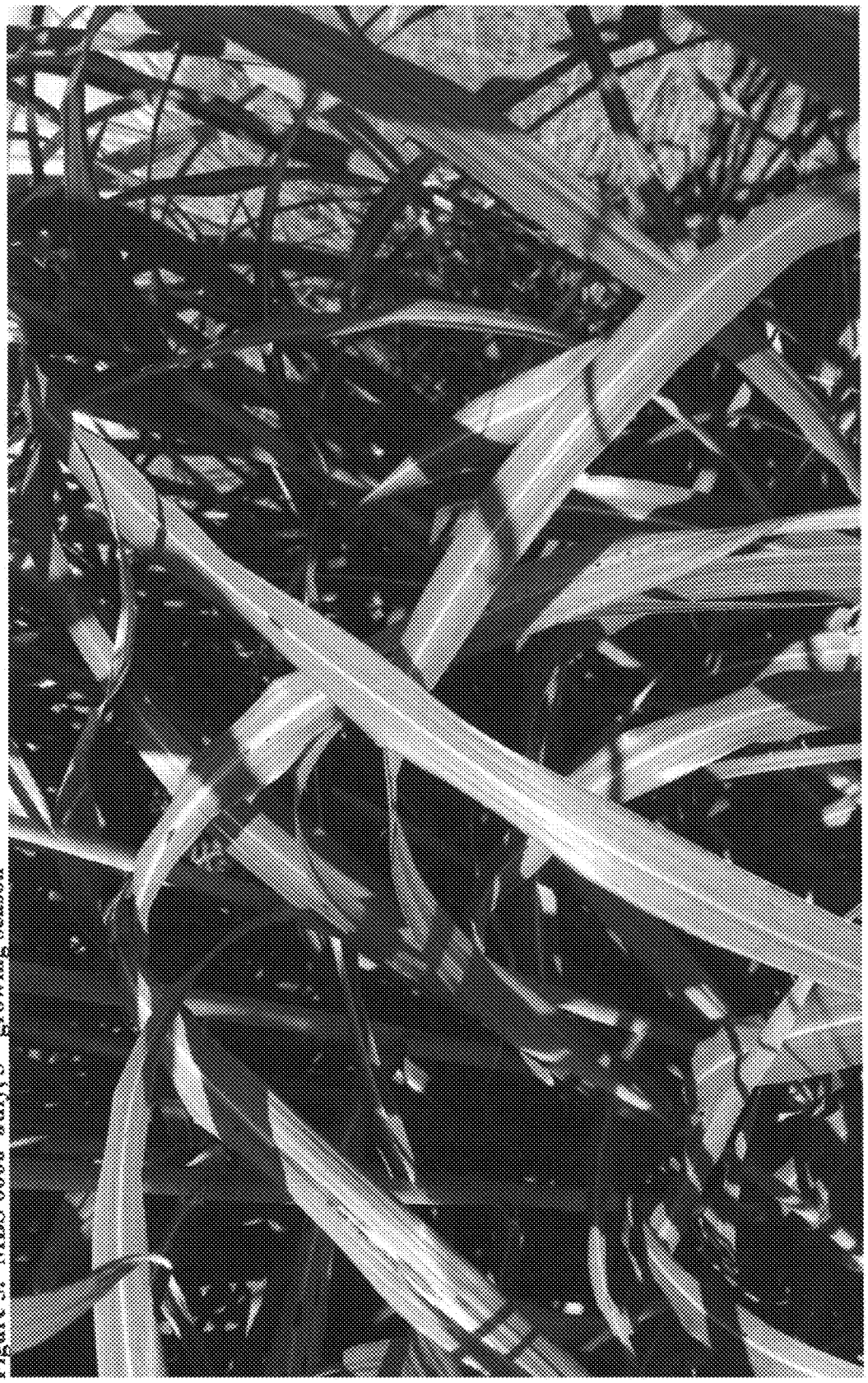
Figure 3. 'MBS 0006' July, 3rd growing season

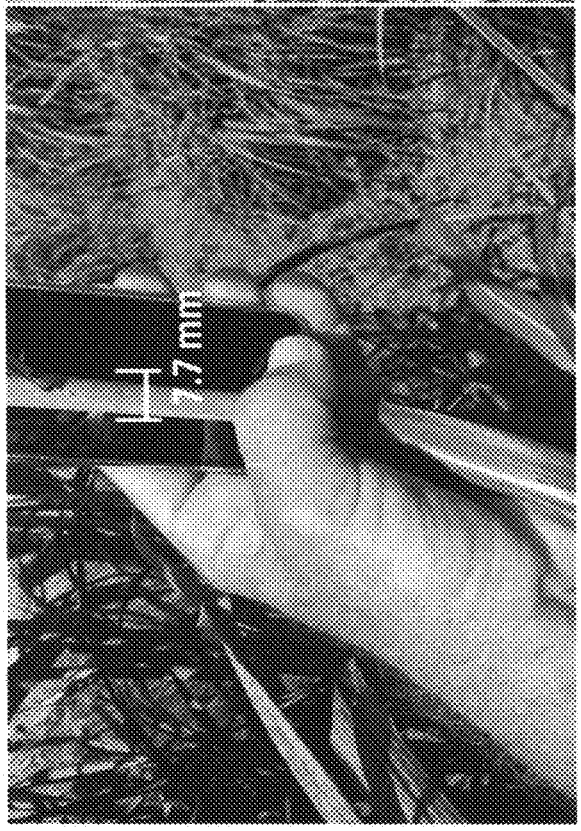
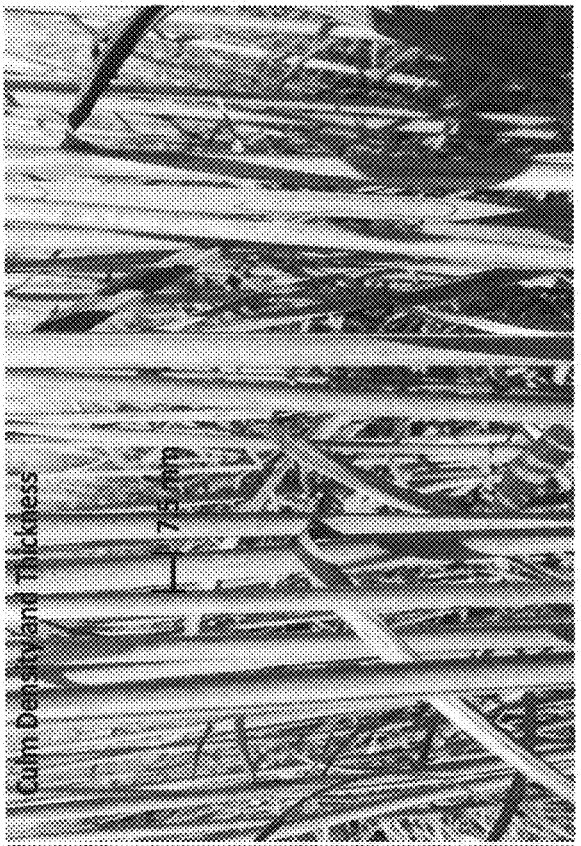
Figure 4 and Figure 5. 'MBS 0006' culm diameter. 3rd growing season

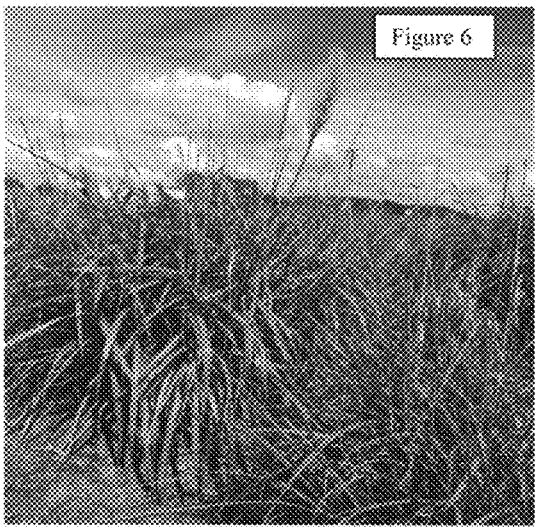
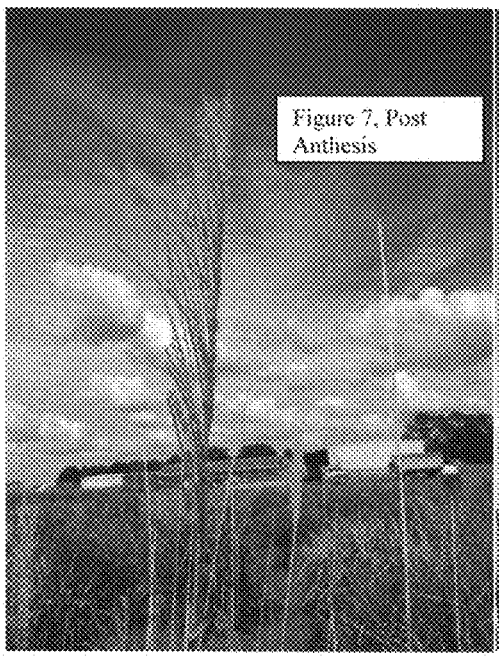
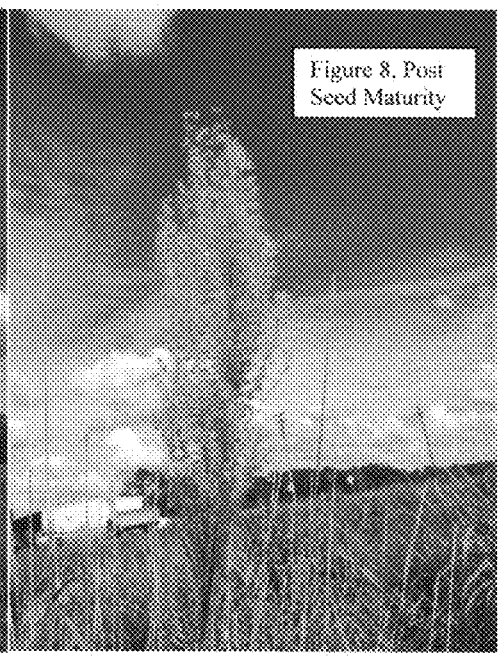

Figures 6, 7, and 8. 'MBS 0006' full plant and inflorescence July, 3rd year growing season.